US012264356B2

(12) United States Patent
Takayama et al.

(10) Patent No.: US 12,264,356 B2
(45) Date of Patent: Apr. 1, 2025

(54) METHOD FOR DETERMINING SENSITIVITY TO SGLT2 INHIBITOR AND SENSITIVITY MARKER FOR SGLT2 INHIBITOR

(71) Applicants: NIHON UNIVERSITY, Tokyo (JP); OSAKI CITY, Osaki (JP); NIPPON KAYAKU KABUSHIKI KAISHA, Tokyo (JP)

(72) Inventors: Tadateru Takayama, Tokyo (JP); Masahiro Usui, Miyagi (JP); Keiko Kudo, Tokyo (JP)

(73) Assignees: NIHON UNIVERSITY, Tokyo (JP); OSAKI CITY, Osaki (JP); NIPPON KAYAKU KABUSHIKI KAISHA, Tokyo (JP)

( * ) Notice: Subject to any disclaimer, the term of this patent is extended or adjusted under 35 U.S.C. 154(b) by 764 days.

(21) Appl. No.: 16/799,064

(22) Filed: Feb. 24, 2020

(65) Prior Publication Data
US 2020/0347458 A1 Nov. 5, 2020

(30) Foreign Application Priority Data
Feb. 25, 2019 (JP) ................................ 2019-031366

(51) Int. Cl.
*C12Q 1/26* (2006.01)
*C12Q 1/6886* (2018.01)

(52) U.S. Cl.
CPC ............. *C12Q 1/26* (2013.01); *C12Q 1/6886* (2013.01); *C12Q 2600/106* (2013.01); *C12Q 2600/158* (2013.01); *C12Q 2600/16* (2013.01); *G01N 2800/042* (2013.01); *G01N 2800/52* (2013.01)

(58) Field of Classification Search
CPC .. C12Q 2600/158; C12Q 1/6886; C12Q 1/26; C12Q 2600/106; C12Q 2600/16; G01N 2800/042; G01N 2800/52; G01N 33/566; G01N 33/6893
See application file for complete search history.

(56) References Cited

U.S. PATENT DOCUMENTS

2010/0047762 A1* 2/2010 Button ............... G01N 33/5088 435/4
2015/0104881 A1 4/2015 Chen et al.

FOREIGN PATENT DOCUMENTS

| JP | 2812676 | B2 | 10/1998 |
| JP | 2001116756 | A | 4/2001 |
| JP | 4544598 | B2 | 9/2010 |
| JP | 5301156 | B2 | 9/2013 |
| JP | 201930821 | A | 2/2019 |

OTHER PUBLICATIONS

Nowatzke et al. "Evaluation of an assay for serum 1,5-anhydoglucitol (GlycoMark) and determination of reference intervals on Hitachi 917 analyzer". Clinica Chimica Acta 350. (2004) 201-209. (Year: 2004).*
Inagaki et al. "Efficacy and safety of canagliflozin alone or as add-on to other oral antihyperglycemic drugs in Japanese patients with type 2 diabetes: A 52-week open-label study". J Diabetes Invest (2015) vol. 6: 210-218 (Year: 2015).*
Elkinson et al. "Canagliflozin: First Global Approval". Drugs. (2013) vol. 73: 979-988 (Year: 2013).*
Balis "Effect of canagliflozin, a sodium-glucose cotransporter 2 inhibitor, on measurement of serum 1,5-anhydroglucitol" Journal of Diabetes (2014) vol. 6: 378-381 (Year: 2014).*
Balis et al., "Effect of canagliflozin, a sodium-glucose cotransporter 2 inhibitor, on measurement of serum 1,5-anhydroglucitol", *Journal of Diabetes 6*, 2014, pp. 378-380.
"Certificate for seeking Application of Provision of Exception to Lack of Novelty of Invention" for the corresponding Japanese Patent Application No. 2019-031366 filed with Japanese Patent Office on Mar. 27, 2019, disclosing four public disclosures.
Takayama, Abstract a90069 of The 82nd Annual Scientific Meeting of the Japanese Circulation Society published at http://www2.convention.co.jp/ics2018/abstracts/ and http://www2.convention.co.jp/ics2018/, published on Feb. 26, 2018.
Takayama, Presentation materials at Luncheon Seminar 54 of the 82nd Scientific Meeting of the Japanese Society of Cardiology on Mar. 25, 2018.
Usui et al., "Diabetes", *Journal of the Japan Diabetes Society*, vol. 61, Supplement 1 2018, Apr. 25, 2018, pp. S-231, II-7-12.
Usui et al., Presentation materials at the 61st Annual Academic Meeting of the Japanese Society of Diabetes Medicine published on May 25, 2018.
Japanese Office Action mailed Jul. 4, 2023 for the corresponding Japanese Patent Application No. 2020-028154 (14 pages including English translation).
Kohan et al., "Long-term study of patients with type 2 diabetes and moderate renal impairment shows that depagliflozin reduces weight and blood pressure but does not improve glycemic control", Clinical Trial, 2014, vol. 85, No. 4, pp. 962-971 (10 pages).
Kashiwagi et al., "A randomized, double-blind, placebo-controlled study on long-term efficacy and safety of ipragliflozin treatment in patients with type 2 diabetes mellitus and renal impairment: results of the Long-Term ASP1941 Safety Evaluation in Patients with Type 2 Diabetes with Renal Impairment (LANTERN) study", 2015, Diabetes, Obesity and Metabolism, vol. 17, No. 2, pp. 152-160 (9 pages).

(Continued)

*Primary Examiner* — Nancy J Leith
*Assistant Examiner* — Kelly Nichet Hassell
(74) *Attorney, Agent, or Firm* — Leason Ellis LLP; Jordan Garner; Mitsuhiro Haraguchi (57) ABSTRACT

The object of the present invention is to provide a method for determining the sensitivity of a subject to an SGLT2 inhibitor, and a sensitivity marker for the SGLT2 inhibitor. The present invention provides a method for determining the sensitivity of a subject to an SGLT2 inhibitor, comprising measuring a biomarker in the biological sample of a subject, and determining the sensitivity of the subject to the SGLT2 inhibitor using the measured biomarker value as an indicator.

14 Claims, 4 Drawing Sheets

(56) References Cited

OTHER PUBLICATIONS

Kim, et al., "Serum 1,5-Anhydroglucitol Concentrations Are a Reliable Index of Glycemic Control in Type 2 Diabetes With Mild or Moderate Renal Dysfunction", Diabetes Care, 2012, vol. 35, pp. 281-286 (6 pages).
Rebholz, "Serum Levels of 1,5-Anhydroglucitol and Risk of Incident End-Stage Renal Disease", American Journal of Epidemiology, 2017, vol. 186, No. 8, pp. 952-960 (9 pages).
Okamoto, "Purity and oral diabetic medicine", Japan Physicians Association Magazine, 2016, vol. 30, No. 5, pp. 575-581 (7 pages) (No translation is submitted. See English translation of Japanese Office Action (Non-Patent Literature Document 1) for relevancy).
Shimizu et al., "Serum concentration and renal handling of 1,5-anhydro-D-glucitol in patients with chronic renal failure" Ann Clin Biochem, 1999, vol. 36, pp. 749-754 (6 pages).
Yamanouchi et al., "Reduction and Recovery of Plasma 1,5-Anhydro-D-Glucitol Level in Diabetes Mellitus", Diabetes, 1987, vol. 36, pp. 709-715 (7 pages).
Yamanouchi et al., "Comparison of 1,5-Anhydroglucitol, HbA1c, and Fructosamine for Detection of Diabetes Mellitus", Diabetes, 1991, vol. 40, pp. 52-57 (6 pages).

\* cited by examiner

FIG. 1

Histgram of 1,5-AG values before and after administration of SGLT2 inhibitor

FIG. 2

1,5-AG values in SGLT2 inhibitor effective group and SGLT2 inhibitor non-effective group before administration of SGLT2 inhibitor

FIG. 3

Ability of 1,5-AG value to diagnose effective group before administration of SGLT2 inhibitor (ROC curve)

FIG. 4

Comparison of HbA1c improvement rates using 1,5-AG values before administration of SGLT2 inhibitor

METHOD FOR DETERMINING SENSITIVITY TO SGLT2 INHIBITOR AND SENSITIVITY MARKER FOR SGLT2 INHIBITOR

This application claims the benefit of Japanese Patent Application No. 2019-031366 filed Feb. 25, 2019, which is incorporated herein by reference in its entirety.

FIELD OF THE INVENTION

The present invention relates to a method for determining a sensitivity of a subject to an SGLT2 inhibitor, which comprises determining a sensitivity of a subject to an SGLT2 inhibitor, using the biomarker value in the biological sample of the subject as an indicator. The present invention further relates to a sensitivity marker for an SGLT2 inhibitor.

BACKGROUND OF THE INVENTION

The SGLT2 (sodium glucose co-transporter type 2) inhibitor has been discovered as an antidiabetic agent in Japan, and at present, it has been developed and has been on the market over the world. The SGLT2 inhibitor specifically inhibits SGLT2 existing in the kidney and thereby suppresses glucose reabsorption in the kidney. Glucose in blood is filtrated in the kidney and is reabsorbed via a transporter (SGLT2, etc.) existing in the renal uriniferous tubule. The SGLT2 inhibitor inhibits this reabsorption by antagonizing with glucose, and as a result, glucose is excreted in urine, so that the blood glucose level is decreased.

Meanwhile, examples of known diabetes markers may include blood glucose level, hemoglobin A1c (HbA1c), glycoalbumin (GA), fructosamine, and 1,5-anhydroglucitol (hereinafter also referred to as "1,5-AG").

1,5-AG is a naturally occurring polyol. 1,5-AG is hardly biosynthesized or metabolized in a human body, and is mainly absorbed with food in the intestines and is excreted from the kidney, so that the 1,5-AG level is kept almost constant in the body. Since 1,5-AG has a structure similar to glucose, the absorption and excretion thereof are carried out by a glucose transporter. In particular, it is considered that 1,5-AG is reabsorbed from urine, mainly mediated by SGLT4 present on the renal uriniferous tubule. When an excessive amount of glucose is present in urine in the case of diabetes, such reabsorption of 1,5-AG is inhibited by glucose, and thus, 1,5-AG is excreted into urine. As such, utilizing the phenomenon that the blood 1,5-AG value decreases in response to the appearance of urinary sugar, 1,5-AG has been used as a marker for grasping the symptoms of diabetes. Reagents for measuring 1,5-AG as a diabetes marker have been developed, and have been on sale as extracorporeal diagnostic products (Lana 1,5AG Auto Liquid, manufactured by Nippon Kayaku Co., Ltd.; and Determiner L 1,5-AG, manufactured by Kyowa Medex Co., Ltd.). Japanese Patent No. 2812676, Japanese Patent No. 4544598 and Japanese Patent No. 5301156 disclose a reagent kit for quantifying 1,5-anhydroglucitol, a kit for measuring 1,5-anhydroglucitol, and a method of measuring 1,5-anhydroglucitol.

Object to be Solved by the Invention

As described above, 1,5-AG has been used as a blood glucose index. In the case of using the SGLT2 inhibitor, due to the mechanism of the SGLT2 inhibitor, the 1,5-AG value is assumed to decrease regardless of the blood glucose level. Therefore, in the case of using the SGLT2 inhibitor, the significance of measuring the 1,5-AG value for the control of diabetes has not been studied. For example, as described in D. A. Balis et al., J. Diabetes, 2014, vol. 6, pp. 378-381 have measured the 1,5-AG value in the blood of patients, to whom an SGLT2 inhibitor, canagliflozin hydrate had been administered, and have reported the obtained results. They have concluded that 1,5-AG would be likely to provide inaccurate results as a blood glucose index in the case of such SGLT2 inhibitor-administered patients. Moreover, although the SGLT2 inhibitor has been used as an antidiabetic agent, a method for determining the sensitivity of a subject to an SGLT2 inhibitor has not yet been known. It is an object of the present invention to provide a clinically applicable method for determining the sensitivity of a subject to an SGLT2 inhibitor, and a sensitivity marker for the SGLT2 inhibitor.

SUMMARY OF THE INVENTION

Means for Solving the Object

As a result of intensive studies directed towards achieving the aforementioned object, the present inventors have found that a biomarker in the biological sample of a subject is measured, and that the sensitivity of the subject to an SGLT2 inhibitor can be determined using the measured biomarker value as an indicator, thereby completing the present invention.

Specifically, according to the present invention, the following inventions are provided.

<1> A method for treating diabetes comprising measuring a biomarker in the biological sample of a subject to determine a sensitivity of the subject to an SGLT2 inhibitor using the measured biomarker value as an indicator, and administering the SGLT2 inhibitor to the subject which was determined to have a sensitivity to the SGLT2 inhibitor.

<2> A method for determining a sensitivity to an SGLT2 inhibitor comprising measuring a biomarker in the biological sample of a subject and using the measured biomarker value as an indicator; or a method for determining the sensitivity of a subject to an SGLT2 inhibitor, comprising measuring a biomarker in the biological sample of a subject, and determining the sensitivity of the subject to the SGLT2 inhibitor using the measured biomarker value as an indicator.

<3> The method according to <1> or <2>, wherein the biomarker is 1,5-anhydroglucitol.

<4> The method according to any one of <1> to <3>, wherein the biological sample is blood.

<5> The method according to any one of <1> to <4>, wherein the biological sample is derived from a subject who does not take the SGLT2 inhibitor, regardless of whether or not the subject takes other antidiabetic agents.

<6> The method according to <5>, wherein when the biomarker is 1,5-anhydroglucitol, the biological sample is the blood of a subject who does not take the SGLT2 inhibitor, and the measured biomarker value is 5 μg/mL or less, the subject is determined to have high sensitivity to the SGLT2 inhibitor.

<7> The method according to <5>, wherein when the biomarker is 1,5-anhydroglucitol, the biological sample is the blood of a subject who does not take the SGLT2 inhibitor, and the measured biomarker value is 7.5 to 10 μg/mL or more, the subject is determined to have low sensitivity to the SGLT2 inhibitor.

<8> The method according to any one of <1> to <4>, wherein the biological sample is derived from a subject who takes an antidiabetic agent other than the SGLT2 inhibitor.
<9> The method according to <8>, wherein when the biomarker is 1,5-anhydroglucitol, the biological sample is the blood of a subject who takes an antidiabetic agent other than the SGLT2 inhibitor, and the measured biomarker value is 5 μg/mL or less, the subject is determined to have high sensitivity to the SGLT2 inhibitor.
<10> The method according to <8>, wherein when the biomarker is 1,5-anhydroglucitol, the biological sample is the blood of a subject who takes an antidiabetic agent other than the SGLT2 inhibitor, and the measured biomarker value is 7.5 to 10 μg/mL or more, the subject is determined to have low sensitivity to the SGLT2 inhibitor.
<11> The method according to any one of <8> to <10>, wherein the antidiabetic agent other than the SGLT2 inhibitor is a sulfonylurea drug, a DPP-4 inhibitor, a thiazolidine drug, or metformin.
<12> The method according to any one of <1> to <4>, wherein the sensitivity of the subject to the SGLT2 inhibitor is determined, using, as an indicator, the biomarker value obtained after the taking of the SGLT2 inhibitor.
<13> The method according to <12>, wherein the sensitivity to the SGLT2 inhibitor is determined, using, as an indicator, the 1,5-anhydroglucitol value obtained 1 week or more after initiation of the taking of the SGLT2 inhibitor.
<14> The method according to <12> or <13>, wherein when the 1,5-anhydroglucitol value obtained 1 week or more after initiation of the taking of the SGLT2 inhibitor is 2 μg/mL or more, the subject is determined to have low sensitivity to the SGLT2 inhibitor.
<15> The method according to any one of <1> to <4>, wherein decreasing of the effects of the SGLT2 inhibitor is determined using, as an indicator, a change in the biomarker value obtained after initiation of the taking of the SGLT2 inhibitor.
<16> The method according to <15>, wherein the change in the biomarker value obtained after initiation of the taking of the SGLT2 inhibitor is an increase in 1,5-anhydroglucitol value.
<17> The method according to <15>, wherein decreasing of the effects of the SGLT2 inhibitor is determined using, as an indicator, the 1,5-anhydroglucitol value obtained after initiation of the taking of the SGLT2 inhibitor that is 2 μg/mL or more.

In the aforementioned method of the present invention, the subject is preferably a diabetes patient.
<18> The method for determining a sensitivity to an SGLT2 inhibitor according to any one of <1> to <17>, wherein 1,5-anhydroglucitol in a biological sample of a subject is measured by using a reagent for quantifying 1,5-anhydroglucitol which comprises pyranose oxidase or L-sorbose oxidase or 1,5-anhydroglucitol dehydrogenase or 1,5-anhydroglucitol-6-phosphate dehydrogenase, and the measured 1,5-anhydroglucitol value is used as an indicator to determine the sensitivity to the SGLT2 inhibitor.
<19> A kit for determining a sensitivity to an SGLT2 inhibitor for use in the method according to any one of <1> to <18>.
<20> The kit for determining the sensitivity of a subject to an SGLT2 inhibitor according to <19>, wherein the kit comprises a reagent for quantifying 1,5-anhydroglucitol that quantifies 1,5-anhydroglucitol or a derivative thereof, using pyranose oxidase or L-sorbose oxidase or 1,5-anhydroglucitol dehydrogenase or 1,5-anhydroglucitol-6-phosphate dehydrogenase.

<21> The kit for determining the sensitivity of a subject to an SGLT2 inhibitor according to <19>, wherein the kit comprises pyranose oxidase (PROD), peroxidase (POD), and coloring reagents.
<22> The kit for determining the sensitivity of a subject to an SGLT2 inhibitor according to <21>, wherein the coloring reagents are 4-aminoantipyrine (4-AAP) and N-ethyl-N-(2-hydroxy-3-sulfopropyl)-3-methylaniline sodium dihydrate (TOOS).
<23> A sensitivity marker for SGLT2 inhibitor which comprises 1,5-anhydroglucitol.

Advantageous Effects of Invention

According to the present invention, the sensitivity of a subject to an SGLT2 inhibitor can be simply determined.

DETAILED DESCRIPTION OF THE INVENTION

Hereinafter, the present invention will be described in more detail.

The method for determining the sensitivity of a subject to an SGLT2 inhibitor according to the present invention comprises measuring a biomarker in the biological sample of a subject, and determining the sensitivity of the subject to the SGLT2 inhibitor using the measured biomarker value as an indicator.

The subject is not particularly limited, and a subject in need of determining the sensitivity thereof to an SGLT2 inhibitor is preferable. Since the SGLT2 inhibitor has been currently used as an antidiabetic agent, the subject is preferably a diabetes patient.

The biological sample is not particularly limited, and examples of the biological sample may include blood, interstitial fluid, saliva, tear, sweat, and urine. Among these, blood, urine, or the like is preferable. The blood may be blood derived from all types of tissues. In general, peripheral blood is preferable. As a method of collecting blood, a common method (e.g., venous blood sampling, fingersticks, etc.) can be applied. The collected blood may be directly used, or a liquid component (plasma) separated from cellular components (erythrocytes, leukocytes, platelets, etc.) according to a common method (e.g., centrifugation, filtration, etc.) may also be used. Moreover, a liquid component (serum) obtained by coagulating blood and then separating platelets or coagulation factors from the blood may also be used.

The biological sample may be derived from a subject who does not take the SGLT2 inhibitor, or may also be derived from a subject who takes the SGLT2 inhibitor.

Moreover, the biological sample may be derived from a subject who takes an antidiabetic agent other than the SGLT2 inhibitor, or may also be derived from a subject who does not take such an antidiabetic agent other than the SGLT2 inhibitor.

Examples of such an antidiabetic agent other than the SGLT2 inhibitor may include: oral drugs, such as sulfonylurea drugs (e.g., glibenclamide, gliclazide, glimepiride, etc.), DPP-4 inhibitors (e.g., sitagliptin phosphate hydrate, vildagliptin, alogliptin benzoate, linagliptin, teneligliptin hydrobromide hydrate, anagliptin, saxagliptin hydrate, trelagliptin, omarigliptin, etc.), thiazolidine drugs (e.g., pioglitazone hydrochloride, etc.), biguanides (e.g., metformin hydrochloride, buformin hydrochloride, etc.), glinide (e.g., nateglinide, mitiglinide calcium hydrate, repaglinide), and α-glucosidase inhibitors (e.g., acarbose, voglibose, miglitol, etc.); and injections such as insulin and GLP-1 receptor agonists (e.g., liraglutide, exenatide, etc.). Among the above-described drugs, preferred examples of the antidiabetic agent other than the SGLT2 inhibitor may include a sulfonylurea drug, a DPP-4 inhibitor, a thiazolidine drug, and metformin.

The biomarker measured in the present invention is not particularly limited, as long as the sensitivity of a subject to an SGLT2 inhibitor can be determined using the measured value as an indicator. In the Examples of the present invention, 1,5-anhydroglucitol was discovered as a marker capable of determining such sensitivity to the SGLT2 inhibitor.

The measurement of such a biomarker can be carried out according to a common method. When 1,5-anhydroglucitol is used as a biomarker, the method of measuring 1,5-anhydroglucitol is not particularly limited, and known methods described in publications can be applied. For example, the 1,5-anhydroglucitol can be measured according to the methods described in Japanese Patent No. 2812676, Japanese Patent No. 4544598 and Japanese Patent No. 5301156. Alternatively, 1,5-anhydroglucitol can also be measured using commercially available diagnostic agents such as Lana (registered trademark) 1,5AG Auto Liquid (manufactured by Nippon Kayaku Co., Ltd.) and Determiner (registered trademark) L 1,5-AG (manufactured by Kyowa Medex Co., Ltd.). Moreover, 1,5-anhydroglucitol can also be measured using diagnostic agents that are sold in some countries, such as Gcell 1,5-anhydroglucitol (Beijing Strong Biotechnologies, Inc.) and Diazyme 1,5-anhydroglucitol assay (Diazyme Laboratories Inc.).

Examples of the SGLT2 inhibitor may include ipragliflozin L-proline (Suglat (registered trademark)), dapagliflozin propylene glycolate hydrate (Forxiga (registered trademark)), luseogliflozin hydrate (Lusefi (registered trademark)), tofogliflozin hydrate (Apleway (registered trademark) and DEBERZA (registered trademark)), canagliflozin hydrate (CANAGLU (registered trademark)), and empagliflozin (Jardiance (registered trademark)). In addition, examples of a combination drug of such an SGLT2 inhibitor and other antidiabetic agents may include a canagliflozin/teneligliptin combination tablet (Tenelia (registered trademark) COMBINATION TABLETS), a ipragliflozin/sitagliptin combination tablet (SUJANU (registered trademark) combination tablets), and an empagliflozin/linagliptin combination tablet (Tradiance (registered trademark) Combination Tablets AP). Furthermore, the SGLT2 inhibitor is not particularly limited, as long as it has an ability to inhibit SGLT2. Thus, the SGLT2 inhibitor also includes an inhibitor that inhibits SGLT1 as well as SGLT2.

In the present invention, using the measured biomarker value as an indicator, the sensitivity of a subject to an SGLT2 inhibitor is determined.

In the present invention, the term "sensitivity" means that the medicinal effects of the SGLT2 inhibitor can be obtained. For example, when the HbA1c value of a subject after administration of the SGLT2 inhibitor is improved by 10% or more, in comparison to the HbA1c value thereof before administration of the SGLT2 inhibitor, the subject can be determined to have sensitivity to the SGLT2 inhibitor. The reason that a patient has low sensitivity may be caused by the properties of the patient, such that the urinary sugar threshold is high and urinary sugar is hardly excreted. However, when low sensitivity is caused by a reduction in renal function, there may be a case where the blood glucose level has been sufficiently improved by other antidiabetic agents. Thus, the reason of low sensitivity is not limited to specific factors.

In one example of the present invention, when the biomarker is 1,5-anhydroglucitol, the biological sample is the blood of a subject who does not take an SGLT2 inhibitor, and the measured biomarker value is 5 µg/mL or less, the subject can be determined to have high sensitivity to the SGLT2 inhibitor. When the biomarker is 1,5-anhydroglucitol, the biological sample is the blood of a subject who does not take an SGLT2 inhibitor, and the measured biomarker value is 7.5 to 10 µg/mL or more, the subject can be determined to have low sensitivity to the SGLT2 inhibitor.

In another example of the present invention, when the biomarker is 1,5-anhydroglucitol, the biological sample is the blood of a subject who does not take an SGLT2 inhibitor but takes an antidiabetic agent other than the SGLT2 inhibitor, and the measured biomarker value is 5 µg/mL or less, the subject can be determined to have high sensitivity to the SGLT2 inhibitor. When the biomarker is 1,5-anhydroglucitol, the biological sample is the blood of a subject who does not take an SGLT2 inhibitor but takes an antidiabetic agent other than the SGLT2 inhibitor, and the measured biomarker value is 7.5 to 10 µg/mL or more, the subject can be determined to have low sensitivity to the SGLT2 inhibitor. An individual biomarker value used as an indicator may be individually set by a doctor depending on the conditions of the patient, the type of an antidiabetic agent used in combination with the SGLT2 inhibitor, or the like.

In a further example of the present invention, the sensitivity of a subject to an SGLT2 inhibitor can be determined, using, as an indicator, the biomarker value obtained after the taking of the SGLT2 inhibitor. That is, the sensitivity of a subject to an SGLT2 inhibitor can be determined, using, as an indicator, the 1,5-anhydroglucitol value obtained 1 week or more after initiation of the taking of the SGLT2 inhibitor. For example, the 1,5-anhydroglucitol value obtained 1 week or more after initiation of the taking of the SGLT2 inhibitor is 2 µg/mL or more, the subject can be determined to have low sensitivity to the SGLT2 inhibitor.

In a further example of the present invention, decreasing of the effects of the SGLT2 inhibitor in a subject can be determined using, as an indicator, a change in the biomarker value obtained after initiation of the taking of the SGLT2 inhibitor. Specifically, the phenomenon that the 1,5-anhydroglucitol value that has been less than 2 µg/mL, for example, is increased to 2 µg/mL or more as a result of the taking of the SGLT2 inhibitor is used as an indicator, and it can be determined that the effects of the SGLT2 inhibitor decreases in the subject. This biomarker value may be individually set by a doctor depending on the conditions of the patient and the like. Such the effects of the SGLT2 inhibitor may decrease by various causes such as changes in the conditions of a patient, such as a urinary sugar threshold or renal function, the influence of other antidiabetic agents, and missing a dose. Thus, the cause of decrease of the effects of the SGLT2 inhibitor is not particularly limited.

According to the present invention, using the measured biomarker value as an indicator, the sensitivity of a subject to an SGLT2 inhibitor can be determined. Therefore, according to the present invention, a subject who can be expected to have the effects of the SGLT2 inhibitor can be efficiently selected. As a result, the SGLT2 inhibitor can be administered to a subject on whom the treatment with the SGLT2 inhibitor can be appropriately carried out.

In the present invention, when a subject has been determined to have sensitivity to an SGLT2 inhibitor, the SGLT2 inhibitor is preferably administered to the subject.

In the present invention, when a subject has been determined not to have sensitivity to an SGLT2 inhibitor, the effects of the SGLT2 inhibitor cannot be expected. When the SGLT2 inhibitor whose effects cannot be expected is continuously administered to the subject, concerns about increased side effects may occur. The method for determining the sensitivity of a subject to an SGLT2 inhibitor according to the present invention also contributes to prevent such increased side effects associated with administration of the SGLT2 inhibitor.

[Kit for Determining Sensitivity to an SGLT2 Inhibitor]

The present invention further relates to a kit for determining the sensitivity of a subject to an SGLT2 inhibitor, for use in the above-described method for determining the sensitivity of a subject to an SGLT2 inhibitor according to the present invention. This kit may be, for example, a kit including a reagent for quantifying 1,5-anhydroglucitol. Examples of the known 1,5-anhydroglucitol quantification method may include an enzyme colorimetric method and an electrochemical method. That is to say, 1,5-anhydroglucitol or a derivative thereof is quantified using pyranose oxidase (PROD), L-sorbose oxidase, 1,5-anhydroglucitol dehydrogenase, 1,5-anhydroglucitol-6-phosphate dehydrogenase, or the like. Further, peroxidase (POD) may also be used. Still further, a coloring reagent may also be used, and examples of the coloring reagent that can be used herein may include oxidative coupling coloring chromogens, oxidative coloring chromogens, and reduced coloring chromogens, which are shown in the following tables. Examples of the oxidative coupling coloring chromogens are shown in Table 1 and Table 2. Any pigment shown in Table 1 can be used in combination with any pigment shown in Table 2. Otherwise, as oxidative coloring chromogens and reduced coloring chromogens, the pigments shown in Table 3 and Table 4 can be used, for example.

In the electrochemical method, an electron-transfer mediator may be used. Examples of the electron-transfer mediator may include ferricyanides, quinone compounds, osmium complexes or the polymer forms thereof, ferrocene compounds, phenothiazine compounds, phenoxazine compounds, phenazine compounds, indophenol compounds, diphenylamine compounds, and phenol compounds, as described in JP Patent Publication (Kokai) No. 2017-134063 A.

TABLE 1

Examples of pigments (oxidative coupling coloring chromogens) that can be used in kit for determining sensitivity to an SGLT2 inhibitor

| Name of Pigment | Abbreviation |
|---|---|
| 4-aminoantipyrine | 4AAP |
| 3-methyl-2-benzothiazolinone hydrazine | MBTH |
| 2-hydrazono-2,3-dihydro-3-methyl-6-benzothiazolesulfonic acid | SMBTH |
| N-methyl-3-methoxy-4'-amino-diphenylamine | NCP-06 |
| N-methyl-4-amino-diphenylamine | NCP-04 |

TABLE 2

Examples of pigments (oxidative coupling coloring chromogens) that can be used in kit for determining sensitivity to an SGLT2 inhibitor

| Name of Pigment | Abbreviation |
|---|---|
| N-ethyl-N-(3-methylphenyl)-N'-succinylethylenediamine | EMSE |
| N-ethyl-N-sulfopropyl-3,5-dimethoxyaniline | DAPS |
| 3-hydroxy-2,4,6-triiodobenzoic acid | HTIB |
| N-ethyl-N-(2-hydroxy-3-sulfopropyl)-3-methoxyaniline | TOOS |
| N-sulfopropylaniline | HALPS |
| N-ethyl-N-sulfopropyl-m-anisidine | ADPS |
| N-sulfopropyl-3,5-dimethoxyaniline | HDAPS |
| N-ethyl-N-sulfopropylaniline | ALPS |
| N-sulfopropyl-3,5-dimethylaniline | MAPS |

TABLE 3

Examples of pigments (oxidative coloring chromogens) that can be used in kit for determining sensitivity to an SGLT2 inhibitor

| Name of Pigment | Abbreviation |
|---|---|
| N-(carboxymethylaminocarbonyl)-4,4'-bis(dimethylamino) diphenylamine sodium salt | DA64 |
| 10-carboxymethylaminocarbonyl-3,7-bis(dimethylamino)phenothiazine sodium salt | DA67 |
| bis[3-bis(4-chlorophenyl)methyl-4-dimethylaminocarboxyethylaminophenyl]amine, 10-N-methylcarbamoyl-3,7-dimethylamino-10H-phenothiazine | MCDP |
| 10-N-carboxymethylcarbamoyl-3,7-dimethylamino-10H-phenothiazine | CCAP |
| 3,3',5,5'-tetramethylbenzidine | TMBZ |
| N,N,N',N',N'',N''-hexa(3-sulfopropyl)-4,4',4''-triaminotriphenylmethane hexasodium salt | TPM-PS |

TABLE 4

Examples of pigments (reduced coloring chromogens) that can be used in kit for determining sensitivity to an SGLT2 inhibitor

| Name of Pigment | Abbreviation |
|---|---|
| Indonitrotetrazolium | INT |
| nitro blue tetrazolium | NBT |
| 2-(4-iodophenyl)-3-(4-nitrophenyl)-5-(2,4-disulfophenyl)-2H-tetrazolium monosodium salt | WST-1 |
| 2-(4-iodophenyl)-3-(2,4-dinitrophenyl)-5-(2,4-disulfophenyl)-2H-tetrazolium monosodium salt | WST-3 |
| 3,3'-[3,3'-dimethoxy-(1,1'-biphenyl)4,4'-diyl]-bis[2-(4-nitrophenyl)-5-phenyl-2H tetrazolium chloride] | NTB |
| 3-(4,5-dimethylthiazole-2-phenyl)-5-(3-carboxymethoxyphenyl)-2-(4-sulfophenyl)-2H-tetrazolium salt | MTS |

The kit for determining the sensitivity of a subject to an SGLT2 inhibitor according to the present invention may include the above-described enzyme, and an appropriately selected coloring reagent or electron-transfer mediator.

Specifically, the present kit preferably includes PROD used as oxidase for 1,5-AG that oxidizes the hydroxyl group at position 2 of 1,5-AG, and a coloring reagent that detects the generated hydrogen peroxide according to a colorimetric method using POD. As such a coloring reagent, a known reagent used in detection of hydrogen peroxide may be adopted, and it is preferable to use, for example, 4-aminoantipyrine (4-AAP) and N-ethyl-N-(2-hydroxy-3-sulfopropyl)-3-methylaniline sodium dihydrate (TOOS).

The kit of the present invention may include constitutional elements other than those as described above, as necessary. Examples of such constitutional elements other than those as described above may include a positive control, a negative control, a calibration standard solution, and instruction manuals describing the method of measuring 1,5-AG using the kit of the present invention. Further, it is preferable to include a description or package insert regarding how to determine the sensitivity to the SGLT2 inhibitor.

According to the present invention, 1,5-anhydroglucitol in the biological sample of a subject is measured using the above-described kit for determining the sensitivity of a subject to an SGLT2 inhibitor, and then, the sensitivity of the subject to the SGLT2 inhibitor can be determined using the measured 1,5-anhydroglucitol value as an indicator.

The present invention will be more specifically described in the following examples. However, these examples are not intended to limit the scope of the present invention.

EXAMPLES

Example 1

Thirty patients suffering from coronary artery disease complicated with type 2 diabetes (28 male patients and 2 female patients; average age: 70.5±8.1 years old) who did outpatient visit and could not sufficiently control their blood glucose level only by administration with an oral hypoglycemic agent were used as subjects. Patients whose casual urinary sugar was positive before administration of the agent were excluded from the subjects. The aforementioned patients were administered with the SGLT2 inhibitor (50 mg Ipragliflozin; 30 cases) alone or in combination with other oral hypoglycemic agents for 3 months. In the additional administration groups, the antidiabetic agents used in combination with the SGLT2 inhibitor were 10 cases of sulfonylurea drugs, 19 cases of DPP-4 inhibitors, 9 cases of thiazolidine drugs, and 4 cases of metformin. The average number of the combined agents was 2.4. During the observation period, the combined antidiabetic agents were not changed.

Before administration of the SGLT2 inhibitor and 3 months after the first administration, 1,5-AG, HbA1c, casual urinary sugar (U-Sugar), LDL cholesterol (LDL-C), hematocrit (Ht), NT-proBNP, and eGFR (estimated glomerular filtration rate) were measured, and changes in individual indicators before and after the administration were examined. Moreover, regarding cases in which the 1,5-AG value before administration of the SGLT2 inhibitor was less than 13 μg/mL (19 male patient cases), changes in individual indicators before and after the administration were examined.

1,5-AG was measured by an enzymatic method (the aforementioned Lana 1,5AG Auto Liquid, manufactured by Nippon Kayaku Co., Ltd.); HbA1c was measured by an HPLC method (manufactured by Tosoh Co., Ltd.); casual urinary sugar was measured by a test paper method (manufactured by Eiken Chemical Co., Ltd.); and LDL cholesterol was measured by an enzymatic method (manufactured by SEKISUI MEDICAL CO., LTD.) and NT-pro BNP was measured by an ELC-EIA method (manufactured by Roche Diagnostics K. K.).

Figure 1:
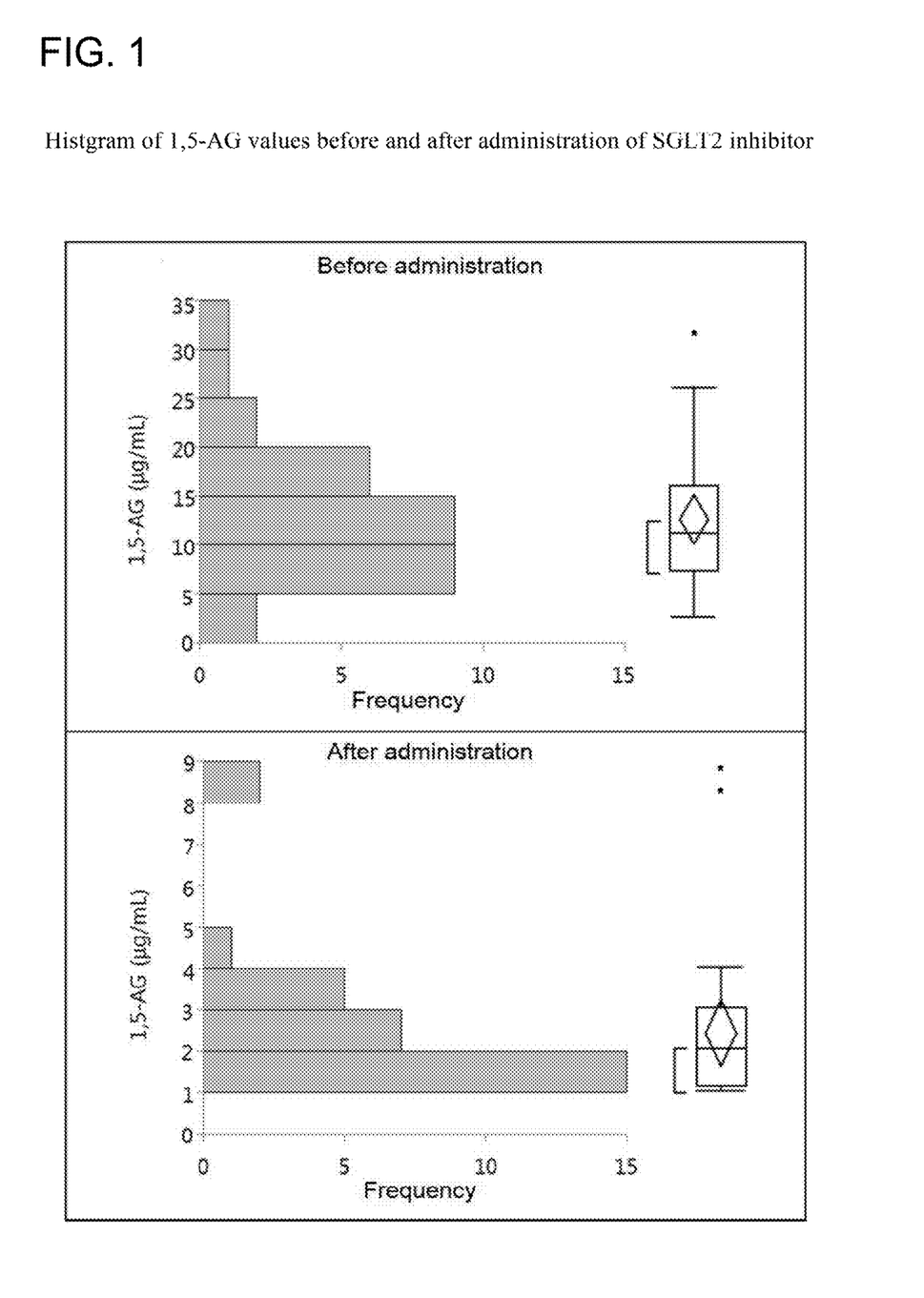
FIG. 1 is a view showing histogram of 1,5-AG values before and after administration of the SGLT2 inhibitor.

The measurement results are shown in Table 5, Table 6, and FIG. 1.

In Table 5 and Table 6, the results are shown with mean±SD, and for statistical analyses, a paired t-test was applied, and p<0.05 was defined to be statistically significant.

TABLE 5

Changes in individual indicators in coronary artery disease patients (30 patients)

| 30 cases (28 male patients and 2 female patients, average age = 70.5 ± 8.1 years old) | Before administration of SGLT2 inhibitor | After administration of SGLT2 inhibitor | P value |
|---|---|---|---|
| 1, 5-AG | 12.8 ± 6.7 | 2.5 ± 2.0 | <0.001 |
| LDL-C | 86.4 ± 18.5 | 97.1 ± 18.4 | <0.001 |
| Ht | 39.8 ± 4.4 | 42.7 ± 4.9 | <0.001 |
| eGFR | 59.8 ± 18.1 | 59.9 ± 18.8 | P = 0.83 |
| NT-proBNP | 225.7 ± 342.1 | 218.2 ± 410.2 | P = 0.75 |
| HbA1c | 7.0 ± 0.8 | 7.2 ± 1.2 | P = 0.40 |
| U-Sugar | (—) | (4+) | <0.001 |

TABLE 6

Changes in individual indicators in patients with
1,5-AG value of less than 13 μg/mL before administration
of SGLT2 inhibitor (19 male patients)

| 19 cases (19 male patients, average age = 70.3 ± 8.5 years old) | Before administration of SGLT2 inhibitor | After administration of SGLT2 inhibitor | P value |
|---|---|---|---|
| 1, 5-AG | 8.6 ± 2.9 | 1.7 ± 0.8 | <0.001 |
| LDL-C | 83.4 ± 14.1 | 95.6 ± 20.1 | <0.001 |
| Ht | 40.1 ± 4.5 | 43.2 ± 5.1 | <0.001 |
| eGFR | 63.0 ± 19.1 | 61.7 ± 19.7 | P = 0.59 |
| NT-proBNP | 248.2 ± 410.0 | 231.8 ± 468.9 | P = 0.55 |
| HbA1c | 7.2 ± 0.8 | 6.8 ± 0.6 | P = 0.13 |
| U-Sugar | (—) | (4+) | <0.001 |

From the above-described results, the significance of measuring 1,5-AG when the SGLT2 inhibitor is not administered may be considered to be the following:
(1) determination of the therapeutic effects in a short term at the initiation of drug therapy or at the time of change of drug therapy,
(2) the grasping of the postprandial hyperglycemia (an abnormal increase in the blood glucose level after meals) of patients with a favorable HbA1c value, and
(3) determination of the therapeutic effects of a drug that improves postprandial hyperglycemia.

Moreover, the significance of measuring 1,5-AG when the SGLT2 inhibitor is administered may be considered to be the following.
(1) Confirmation of the effects of the SGLT2 inhibitor at 1 week after the administration thereof by the measurement of 1,5-AG If the 1,5-AG value at 1 week after the administration of the SGLT2 inhibitor is decreased to approximately 1 μg/mL, it can be determined that urinary sugar is excreted, and that the SGLT2 inhibitor is effective.
(2) Increase in 1,5-AG value during administration Since an increase in the blood 1,5-AG value indicates reabsorption of 1,5-AG via the renal uriniferous tubule, it is considered that the effects of the agent would decrease, such as acceleration of reabsorption of sugar via something other than SGLT2.
(3) Possibility of overeating When HbA1c is deteriorated although a low 1,5-AG value is maintained, there is the possibility of overeating.

Example 2

149 patients suffering from type 2 diabetes (82 male patients and 67 female patients; average age: 56.7±13.4 years old), to whom the SGLT2 inhibitor was newly administered alone or in combination with other hypoglycemic agents, were used as subjects. The follow up for 32 weeks after the administration was observed retrospectively. The background of the patients and the combined agents are as shown in Table 7 and Table 8, and the average number of the combined agents was 2.6. During all agent treatment, initiation, change and suspension of the administration were all implemented according to physicians' decision.

A group, in which HbA1c was improved by 10% or more in comparison to the value before administration until 32 weeks after initiation of the administration and the amount of the agent was not increased, was defined to be an effective group; whereas a group, in which HbA1c was improved by less than 10% in comparison to the value before administration, or the amount of the sulfonylurea drugs or insulin was increased, was defined to be a non-effective group. Differences of the clinical indicator values were examined between the two groups.

With regard to evaluation items, such as age, gender, body weight, HbA1c, glycoalbumin, 1,5-AG, liver function, lipids, eGFR, urinary albumin, and combined agents other than antidiabetic agents, information was collected from patients' medical records. The measurement of the body weight, blood sampling, and urinalysis were carried out at every outpatient visit. Glycoalbumin and 1,5-AG were measured in a commercial laboratory (BML, INC), and other markers were measured in the hospital.

The results are represented with mean±SD, and for statistical analyses regarding comparison between the two groups, a paired t-test was applied, and p<0.001 was defined to be statistically significant.

TABLE 7

Background of target patients (149 cases)

| Item | Mean ± SD |
|---|---|
| Age (years old) | 56.7 ± 13.4 |
| Male/Female | 82/67 |
| Body Weight (kg) | 78.4 ± 17.8 |
| BMI (kg/m^2) | 29.44 ± 5.56 |
| HbA1c (%) | 7.99 ± 1.10 |
| GA (%) | 20.21 ± 5.36 |
| 1,5-AG (μg/mL) | 8.00 ± 6.49 |
| AST (IU/L) | 33.3 ± 23.4 |
| ALT (IU/L) | 40.7 ± 30.5 |
| γGTP (IU/L) | 54.3 ± 56.5 |
| TG (mg/dL) | 178.1 ± 118.7 |
| HDL-C (mg/dL) | 47.6 ± 14.1 |
| LDL-C (mg/dL) | 102.6 ± 31.6 |
| eGFR (ml/min/1.73 m^2) | 81.45 ± 32.88 |

TABLE 8

Combined agents used with SGLT2 inhibitor

| Combined Drug | Percentage (%) |
|---|---|
| Insulin | 38.7 |
| Sulfonylurea drugs | 21.9 |
| Glinides | 6.5 |
| DPP-4 inhibitors | 58.1 |
| GLP-1 receptor agonists | 13.5 |
| Thiazolidine drugs | 12.9 |
| Biguanides | 71.0 |
| α-Glucosidase inhibitors | 16.8 |
| None | 6.5 |

Average number of combined agents: 2.5

Figure 2:
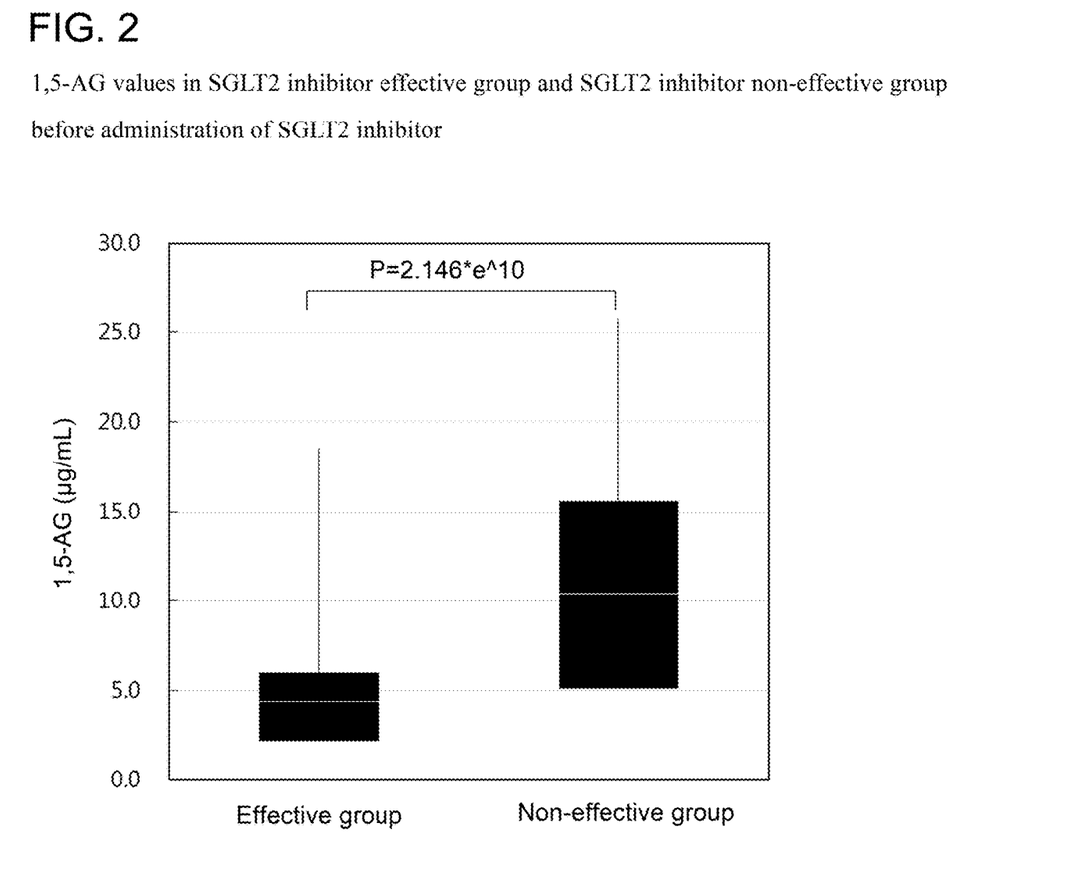
FIG. 2 is a box-and-whisker plot showing 1,5-AG values in an SGLT2 inhibitor effective group and an SGLT2 inhibitor non-effective group before administration of the SGLT2 inhibitor.
Figure 3:
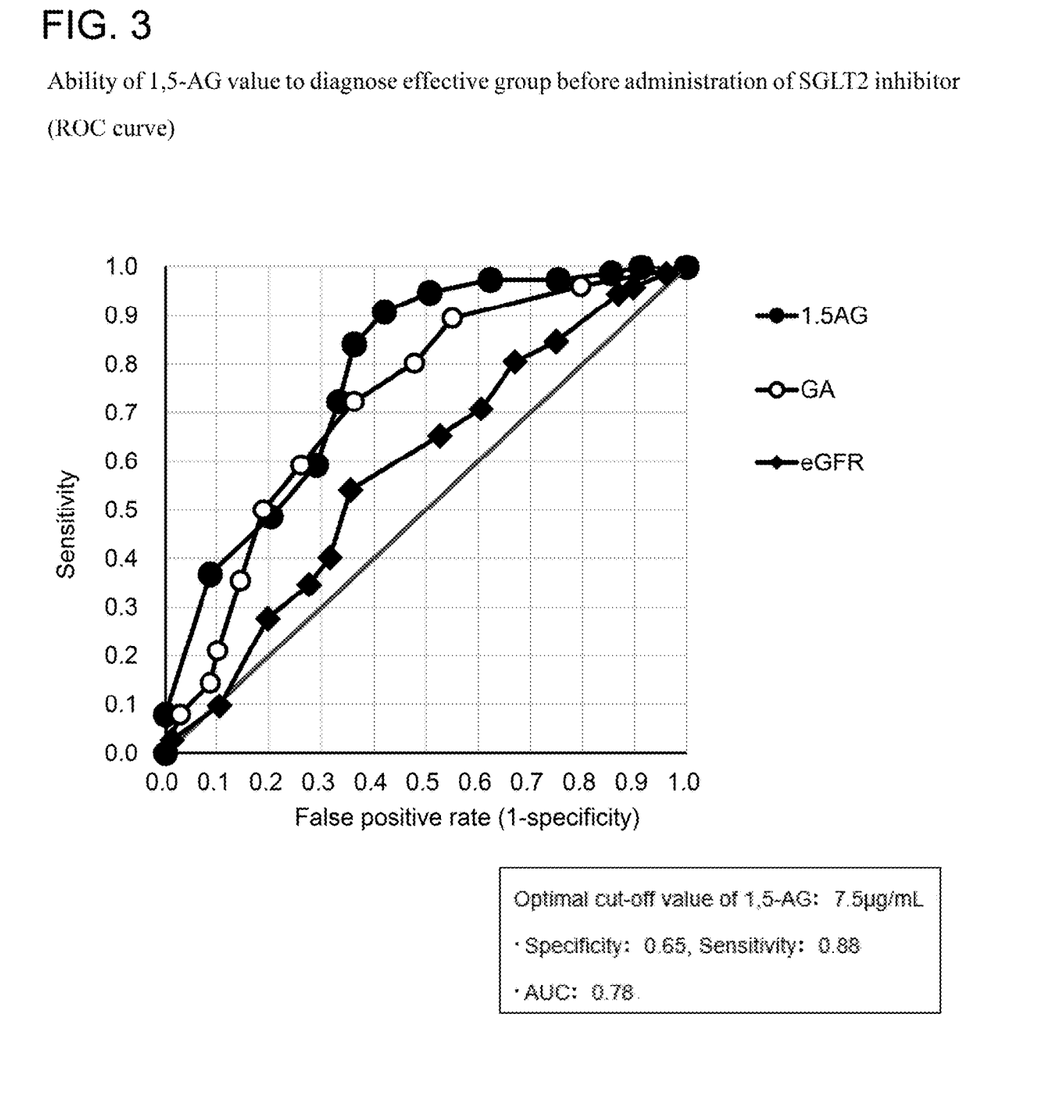
FIG. 3 is an ROC curve obtained when the 1,5-AG value, GA value, and eGFR value before administration of the SGLT2 inhibitor were used in the diagnosis of an SGLT2 inhibitor effective group.
Figure 4:
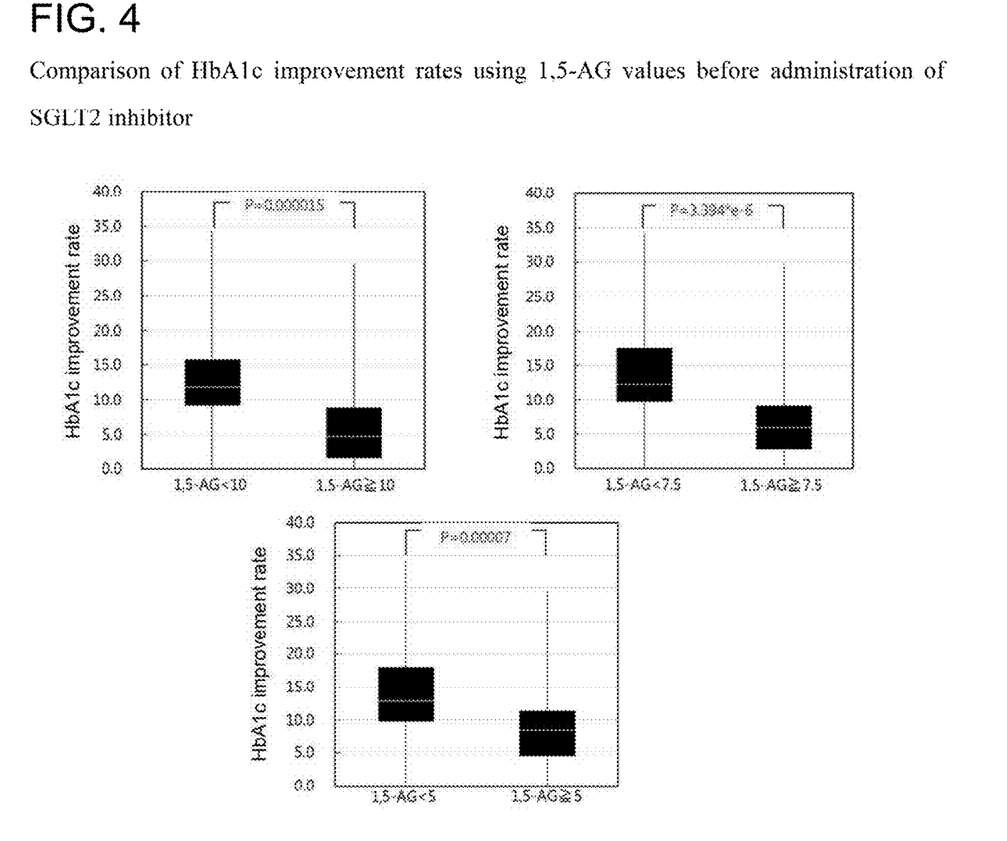
FIG. 4 is a box-and-whisker plot showing HbA1c improvement rates shown with 10 μg/mL, 7.5 μg/mL, and 5 μg/mL cut-off of 1,5-AG values before administration of the SGLT2 inhibitor.

The results are shown in Table 9 and FIGS. 2 to 4. In the effective group, the glycoalbumin (GA) value before administration was significantly higher and the 1,5-AG value before administration was significantly lower, in comparison to the non-effective group. A significant correlation was not found between the results and age, BMI or eGFR, respectively. In addition, in the effective group, ALT (alanine aminotransferase) and γGTP (γ-glutamyl transpeptidase) were also significantly improved. From the ROC curve, 1,5-AG before administration was considered to be the most significant indicator for determination of the effects of the SGLT2 inhibitor. Even in the case of matching with GA, 1,5-AG was the most significant indicator for determination of the effects in the case of administration of the SGLT2 inhibitor. It is considered that, even under the enforcement of diet therapy, by measuring 1,5-AG before administration of the SGLT2 inhibitor, patients in whom data improvement can be expected can be predicted. Moreover, the average HbA1c value of 17 patients, having a 1,5-AG value of 2 µg/mL or more, at 1 year after administration of the SGLT2 inhibitor was 7.18, and thus, the HbA1c value was improved by 0.64 from the value before administration of the SGLT2 inhibitor that was 7.82. Likewise, the average HbA1c value of 10 patients, having a 1,5-AG value of 2.5 µg/mL or more, at 1 year after administration of the SGLT2 inhibitor was 7.15, and HbA1c value was improved by only 0.25 from the value before administration of the SGLT2 inhibitor that was 7.40.

TABLE 9

Mean value (mean ± SD) of each indicator in SGLT2 inhibitor effective group and SGLT2 inhibitor non-effective group before administration

|  | Group in which HbA1c was decreased to 90% or less of previous value (effective group) | Group in which HbA1c was not decreased to 90% or less of previous value (non-effective group) | P value |
|---|---|---|---|
| Number of cases | 77 | 72 |  |
| Male (%) | 53.2 | 56.9 | 0.653 |
| Age (years old) | 57.5 ± 12.7 | 57.0 ± 14.0 | 0.837 |
| BMI (kg/m^2) | 29.62 ± 5.85 | 29.25 ± 5.26 | 0.687 |
| eGFR (mL/min/1.73 m^2) | 84.27 ± 29.22 | 78.47 ± 36.27 | 0.288 |
| HbA1c (%) | 8.62 ± 1.04 | 7.32 ± 0.70 | <0.0001 |
| GA (%) | 21.88 ± 5.76 | 18.37 ± 4.20 | <0.0001 |
| 1,5-AG (µg/mL) | 5.02 ± 3.87 | 11.28 ± 7.20 | <0.0001 |
| AST (IU/L) | 33.6 ± 21.5 | 35.3 ± 24.7 | 0.667 |
| ALT (IU/L) | 43.5 ± 33.5 | 39.6 ± 26.0 | 0.356 |
| γGTP (IU/L) | 58.2 ± 60.3 | 50.9 ± 52.3 | 0.435 |
| TG (mg/dL) | 205.0 ± 145.8 | 150.0 ± 72.8 | 0.004 |
| HDL-C (mg/dL) | 46.94 ± 14.60 | 48.22 ± 13.75 | 0.584 |
| LDL-C (mg/dL) | 105.63 ± 32.63 | 99.39 ± 30.43 | 0.232 |

The invention claimed is:

1. A method for treating diabetes in a subject, the method comprising the steps of:
    measuring a biomarker in a biological sample of the subject to obtain a biomarker value, wherein the subject has not previously taken an SGLT2 inhibitor;
    determining that the subject has a measured biomarker value of 5 µg/ml or less, where an HbA1c value of the subject is expected to decrease by 10% or more after administrating the SGLT2 inhibitor; and
    administering the SGLT2 inhibitor to the subject, wherein the biomarker is 1,5-anhydroglucitol, and the biological sample is blood obtained from the subject.

2. The method according to claim 1, wherein the subject is one who has not taken other antidiabetic agents.

3. The method according to claim 1, further comprising the step of determining that when the measured biomarker value is 7.5 to 10 µg/mL or more, the subject is in a non-effective group where the HbA1c value of the subject is expected to decrease by less than 10% after administrating the SGLT2 inhibitor.

4. The method according to claim 1, wherein the biological sample is derived from the subject who has taken an antidiabetic agent other than the SGLT2 inhibitor.

5. The method according to claim 4, further comprising the step of determining that when the measured biomarker value is 7.5 to 10 µg/mL or more, the subject is in a non-effective group where the HbA1c value of the subject is expected to decrease by less than 10% after administrating the SGLT2 inhibitor.

6. The method according to claim 4, wherein the antidiabetic agent other than the SGLT2 inhibitor is a sulfonylurea drug, a DPP-4 inhibitor, a thiazolidine drug, or metformin.

7. The method according to claim 1, wherein the biomarker value is also obtained after the administration of the SGLT2 inhibitor.

8. The method according to claim 7, wherein the biomarker value is obtained 1 week or more after the administration of the SGLT2 inhibitor.

9. The method according to claim 7, wherein when the biomarker value obtained 1 week or more after the administration of the SGLT2 inhibitor is 2 µg/mL or more, the subject is determined to be in a non-effective group where the HbA1c value of the subject is expected to decrease by less than 10% after administrating the SGLT2 inhibitor.

10. The method according to claim 7, further comprising the step of determining whether or not an effect of the SGLT2 inhibitor decreases based on a change in the biomarker value obtained after the administration of the SGLT2 inhibitor.

11. The method according to claim 10, wherein the change in the biomarker value is an increase in the biomarker value.

12. The method according to claim 10, wherein the effect of the SGLT2 inhibitor is determined to be decreasing when the biomarker value obtained after the administration of the SGLT2 inhibitor that is 2 µg/mL or more.

13. The method according to claim 1, wherein 1,5-anhydroglucitol in the biological sample is measured by using a reagent for quantifying 1,5-anhydroglucitol, said reagent comprising pyranose oxidase, L-sorbose oxidase, 1,5-anhydroglucitol dehydrogenase or 1,5-anhydroglucitol-6-phosphate dehydrogenase.

14. The method according to claim 7, wherein 1,5-anhydroglucitol in the biological sample is measured by using a reagent for quantifying 1,5-anhydroglucitol, said reagent comprising pyranose oxidase, L-sorbose oxidase, 1,5-anhydroglucitol dehydrogenase or 1,5-anhydroglucitol-6-phosphate dehydrogenase.

\* \* \* \* \*